US008929411B1

(12) United States Patent
Safai

(10) Patent No.: US 8,929,411 B1
(45) Date of Patent: Jan. 6, 2015

(54) QUANTUM DOT DETECTION

(71) Applicant: The Boeing Company, Chicago, IL (US)

(72) Inventor: Morteza Safai, Newcastle, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 14/064,657

(22) Filed: Oct. 28, 2013

Related U.S. Application Data

(62) Division of application No. 13/226,750, filed on Sep. 7, 2011, now Pat. No. 8,588,262.

(51) Int. Cl.
H01S 3/10 (2006.01)
H01L 31/0352 (2006.01)

(52) U.S. Cl.
CPC ..... *H01L 31/035218* (2013.01); *Y10S 977/774* (2013.01)
USPC ............. 372/24; 372/23; 324/76.11; 977/774

(58) Field of Classification Search
USPC ................. 372/24, 23; 342/76.11; 977/774
See application file for complete search history.

(56) References Cited

U.S. PATENT DOCUMENTS

| 5,411,890 | A | 5/1995 | Falat |
| 5,429,009 | A | 7/1995 | Wolfe et al. |
| 5,466,605 | A | 11/1995 | Glaunsinger et al. |
| 5,482,890 | A | 1/1996 | Liu et al. |
| 5,763,886 | A * | 6/1998 | Schulte ................. 250/358.1 |
| 6,379,622 | B1 | 4/2002 | Polak et al. |
| 6,421,418 | B1 * | 7/2002 | Schulte ....................... 378/89 |
| 6,564,620 | B1 | 5/2003 | Jaeger |
| 6,627,914 | B1 | 9/2003 | Komiyama et al. |
| 6,657,232 | B2 | 12/2003 | Morkoc |
| 6,710,366 | B1 | 3/2004 | Lee et al. |
| 6,717,664 | B2 | 4/2004 | Floyd et al. |
| 6,843,328 | B2 | 1/2005 | Boyl-Davis et al. |

(Continued)

FOREIGN PATENT DOCUMENTS

| EP | 1130385 | A1 | 9/2001 |
| EP | 1245949 | A2 | 10/2002 |

(Continued)

OTHER PUBLICATIONS

International Search Report, dated Mar. 31, 2010, regarding Application No. PCT/US2009/068223, 5 pages.

(Continued)

*Primary Examiner* — Kinam Park
(74) *Attorney, Agent, or Firm* — Yee & Associates, P.C.

(57) ABSTRACT

An apparatus comprises a laser system and a light sensor system. The laser system is associated with a housing and configured to generate a first laser beam and direct the first laser beam toward a surface of an object in which the surface has a plurality of quantum dots. The first laser beam is configured to cause the plurality of quantum dots to generate light. The laser system is further configured to generate a second laser beam and direct the second laser beam toward the light generated by the plurality of quantum dots. The second laser beam is configured to amplify a portion of the light generated by the plurality of quantum dots. The light sensor system is associated with the housing and configured to detect the portion of the light to form data.

6 Claims, 9 Drawing Sheets

(56) References Cited

U.S. PATENT DOCUMENTS

| | | | |
|---|---|---|---|
| 7,002,079 | B2 | 2/2006 | Mitchell et al. |
| 7,005,669 | B1 | 2/2006 | Lee |
| 7,026,641 | B2 | 4/2006 | Mohseni et al. |
| 7,142,634 | B2 | 11/2006 | Engler et al. |
| 7,212,283 | B2 | 5/2007 | Hother et al. |
| 7,216,408 | B2 | 5/2007 | Boyl-Davis et al. |
| 7,253,004 | B2 | 8/2007 | Vossmeyer et al. |
| 7,304,305 | B2 | 12/2007 | Hunt |
| 7,306,823 | B2 | 12/2007 | Sager et al. |
| 7,342,235 | B1 | 3/2008 | Harrison et al. |
| 7,345,596 | B2 | 3/2008 | Wallach |
| 7,380,776 | B2 | 6/2008 | Boyl-Davis et al. |
| 7,513,941 | B2 | 4/2009 | Frey et al. |
| 7,528,372 | B2 | 5/2009 | Garvey, III et al. |
| 7,529,343 | B2 | 5/2009 | Safai et al. |
| 7,534,489 | B2 | 5/2009 | Ying et al. |
| 7,535,990 | B2 | 5/2009 | Safai et al. |
| 7,567,649 | B1 | 7/2009 | Safai et al. |
| 7,620,150 | B1 | 11/2009 | Annis |
| 7,623,626 | B2 | 11/2009 | Safai et al. |
| 7,649,976 | B2 | 1/2010 | Georgeson et al. |
| 7,780,913 | B2 | 8/2010 | Farmer |
| 7,785,717 | B2 | 8/2010 | Barbera-Guillem |
| 7,807,265 | B2 | 10/2010 | Santra et al. |
| 7,887,938 | B2 | 2/2011 | Fristad et al. |
| 7,902,524 | B2 | 3/2011 | Safai et al. |
| 7,925,452 | B2 | 4/2011 | Safai et al. |
| 7,955,858 | B2 | 6/2011 | Davis et al. |
| 7,976,726 | B2 | 7/2011 | Wang et al. |
| 8,185,326 | B2 | 5/2012 | Safai et al. |
| 8,396,187 | B2 | 3/2013 | Safai et al. |
| 8,503,610 | B1 | 8/2013 | Safai |
| 2002/0104961 | A1 | 8/2002 | Hoffman |
| 2002/0181653 | A1* | 12/2002 | Birdwell et al. ............ 378/58 |
| 2003/0068824 | A1 | 4/2003 | Frankel et al. |
| 2003/0109056 | A1 | 6/2003 | Vossmeyer et al. |
| 2003/0160182 | A1 | 8/2003 | Petrich et al. |
| 2004/0211894 | A1 | 10/2004 | Hother et al. |
| 2005/0109939 | A1 | 5/2005 | Engler et al. |
| 2005/0200481 | A1 | 9/2005 | Wallach |
| 2005/0269127 | A1* | 12/2005 | Mitchell et al. ........... 174/140 C |
| 2005/0277710 | A1* | 12/2005 | Joyce et al. ................ 523/210 |
| 2006/0062902 | A1 | 3/2006 | Sager et al. |
| 2006/0068203 | A1* | 3/2006 | Ying et al. ................. 428/403 |
| 2006/0152706 | A1 | 7/2006 | Butland |
| 2006/0192115 | A1 | 8/2006 | Thomas et al. |
| 2007/0042139 | A1 | 2/2007 | Cooper et al. |
| 2007/0048867 | A1 | 3/2007 | Farmer |
| 2007/0110960 | A1 | 5/2007 | Frey et al. |
| 2007/0189454 | A1 | 8/2007 | Georgeson et al. |
| 2007/0194297 | A1 | 8/2007 | McCarthy et al. |
| 2007/0264719 | A1 | 11/2007 | Santra et al. |
| 2007/0269006 | A1* | 11/2007 | Safai et al. ................ 378/57 |
| 2007/0269014 | A1* | 11/2007 | Safai et al. ................ 378/143 |
| 2008/0050513 | A1 | 2/2008 | Wang et al. |
| 2008/0057304 | A1 | 3/2008 | Fristad et al. |
| 2008/0241071 | A1 | 10/2008 | West et al. |
| 2008/0312847 | A1 | 12/2008 | Safai et al. |
| 2009/0110147 | A1* | 4/2009 | Safai et al. ................ 378/87 |
| 2010/0151577 | A1 | 6/2010 | Davis et al. |
| 2010/0213387 | A1* | 8/2010 | Safai et al. ............... 250/458.1 |
| 2011/0176962 | A1 | 7/2011 | Davis et al. |
| 2012/0148026 | A1 | 6/2012 | Safai |

FOREIGN PATENT DOCUMENTS

| | | |
|---|---|---|
| WO | WO9805946 A1 | 2/1998 |
| WO | WO0214785 A1 | 2/2002 |
| WO | WO2005124340 A1 | 12/2005 |
| WO | WO2006107331 A1 | 10/2006 |
| WO | WO2006107493 A1 | 10/2006 |
| WO | WO2007130545 A2 | 11/2007 |
| WO | WO2007130576 A2 | 11/2007 |
| WO | WO2009055284 A1 | 4/2009 |
| WO | WO2010077930 A1 | 7/2010 |
| WO | WO2012071118 A1 | 5/2012 |

OTHER PUBLICATIONS

International Search Report, dated Jun. 1, 2012, regarding Application No. PCT/US2011/057030, 5 pages.

International Search Report, dated Jan. 19, 2012, regarding Application No. PCT/US2011/057892, 5 pages.

Artemyev et al., "Quantum dots in photonic dots," Applied Physics Letters, vol. 96, Issue 11, Mar. 2000, pp. 1353-1355.

Bakkers et al., "Excited-State Dynamics in CdS Quantum Dots Absorbed on a Metal Electrode," Journal of Physical Chemistry, vol. 103, No. 14, Mar. 1999, pp. 2781-2788.

Bryant et al., "The use of fluorescent probes for the detection of under-film corrosion," Progress in Organic Coatings, vol. 57, Issue 4, Dec. 2006, pp. 416-420.

Dunn, "Flaw detection by X-ray scanning using the rolling-window template-matching procedure," Applied Radiation and Isotopes, vol. 61, No. 6, Dec. 2004, pp. 1217-1225.

Dyba et al., "STED-Microscopy Overcomes the Diffraction Limit in a Fundamental Way", 3 pages. Accessed Aug. 8, 2011, http://www.mpibpc.mpg.de/groups/hell/STED.htm.

Georgeson et al., "X-Ray Backscatter Imaging for Aerospace Applications," Nucsafe Inc. & The Boeing Company, Jul. 22, 2010, 24 pages.

"Group (periodic table)," Wikipedia Foundation, Inc., dated Jun. 15, 2012, 3 pages. Accessed Jun. 15, 2012, http://en.wikipedia.org/wiki/Group_(periodic_table).

Hakim et al., "Nanocoating Individual Silica Nanoparticles by Atomic Layer Deposition in a Fluidized Bed Reactor," Chemical Vapor Deposition, vol. 11, Issue 10, Oct. 2005, pp. 420-425.

"Making Nanodots Useful for Chemistry", ScienceDaily, dated Jun. 19, 2003, 2 pages. Accessed Jun. 15, 2012, http://www.sciencedaily.com/releases/2003/06/030619075658.htm.

Shedlock et al., "X-Ray Backscatter Imaging for Aerospace Applications," AIP Conference Proceedings, vol. 1335, Jun. 2011, pp. 509-516.

"Single Photon Detection," Toshiba Corporation, copyright 1995-2011, 2 pages. Accessed Jun. 15, 2012, http://www.toshiba-europe.com/research/crl/qig/singlephotondetection.html.

"Advantages of quantum dots over conventional fluorophores," University of California-Irvine, Jun. 2007, 2 pages. Accessed Jan. 15, 2012, http://bme240.eng.uci.edu/students/07s/yokabe/advantages.htm.

Westphal et al., "Nanoscale Resolution in the Focal Plane of an Optical Microscope", Physical Review Letters, vol. 94, No. 14, Apr. 2005, 4 pages.

Yu et al., "Experimental determination of the extinction coefficient of CdTe, CdSe, and CdS nanocrystals," Chemistry of Materials, vol. 15, No. 14, Jun. 2003, pp. 2854-2860.

"[3-(2-Aminoethyl)aminopropyl]trimethoxysilane", ScienceLab, copyright 1997-2005, 2 pages. Accessed Jun. 15, 2012, http://www.sciencelab.com/page/S/PVAR/SLA3115.

Office Action, dated Oct. 28, 2009, regarding U.S. Appl. No. 12/335,724, 18 pages.

Office Action, dated Mar. 9, 2010, regarding U.S. Appl. No. 12/335,724, 7 pages.

Final Office Action, dated Aug. 5, 2010, regarding U.S. Appl. No. 12/335,724, 10 pages.

Office Action, dated Feb. 8, 2011, regarding U.S. Appl. No. 12/335,724, 8 pages.

Notice of Allowance, dated Mar. 25, 2011, regarding U.S. Appl. No. 12/335,724, 5 pages.

Office Action, dated Sep. 22, 2011, regarding U.S. Appl. No. 13/070,046, 15 pages.

Office Action, dated Feb. 10, 2012, regarding U.S. Appl. No. 13/070,046, 17 pages.

Final Office Action, dated Jul. 3, 2012, regarding U.S. Appl. No. 13/070,046, 10 pages.

(56) References Cited

OTHER PUBLICATIONS

Office Action, dated Aug. 20, 2010, regarding U.S. Appl. No. 12/390,965, 15 pages.
Notice of Allowance, dated Nov. 3, 2010, regarding U.S. Appl. No. 12/390,965, 7 pages.
Office Action, dated Oct. 12, 2012, regarding U.S. Appl. No. 12/952,652, 27 pages.
Notice of Allowance, dated Mar. 27, 2013, regarding U.S. Appl. No. 12/952,652, 12 pages.
Notice of Allowance, dated Dec. 14, 2012, regarding U.S. Appl. No. 12/965,159, 22 pages.
Safai, "Quantum Dot Detection," U.S. Appl. No. 13/226,750, filed Sep. 7, 2011, 45 pages.
Notice of Allowance, dated Jul. 17, 2013, regarding U.S. Appl. No. 13/226,750, 29 pages.

* cited by examiner

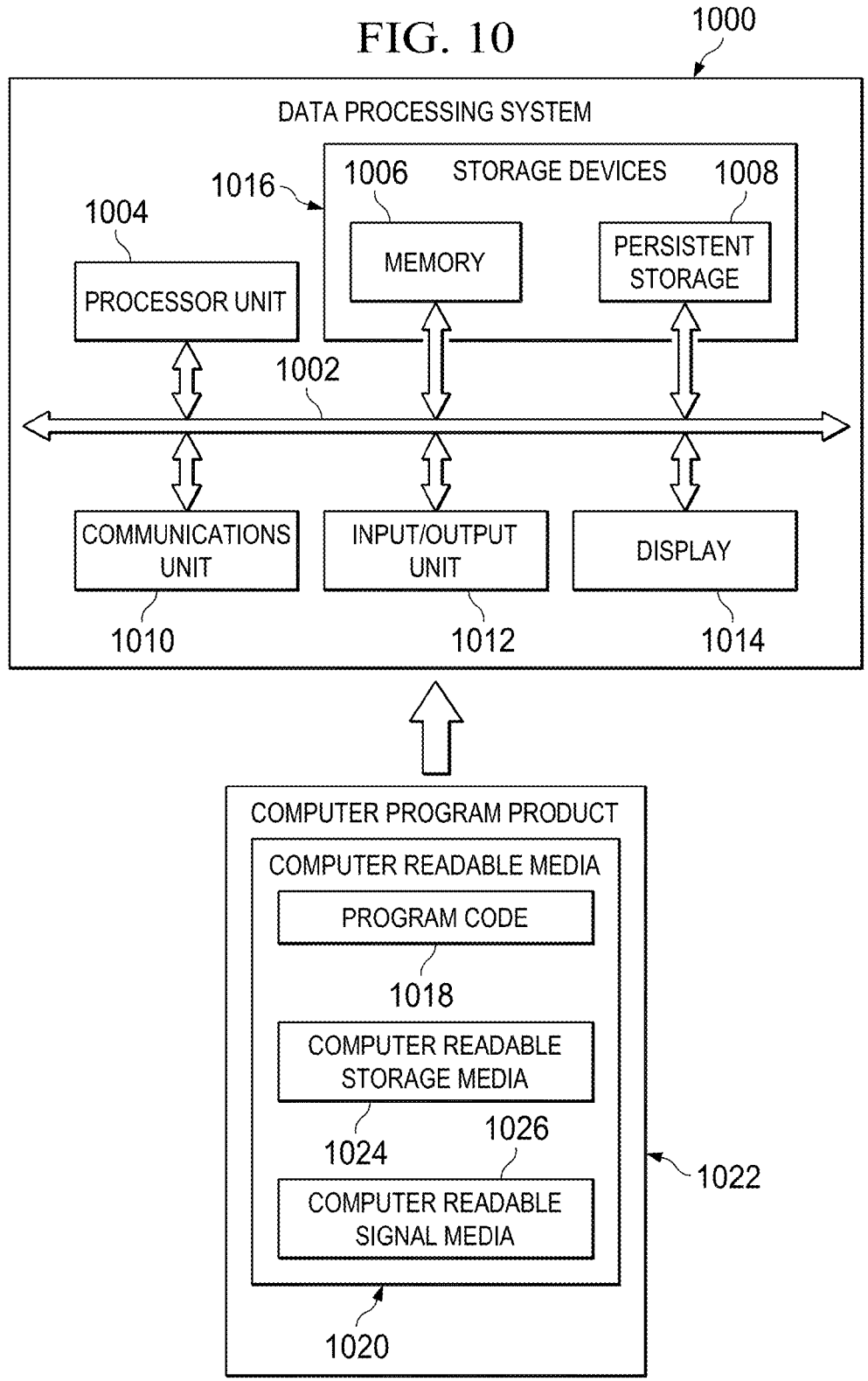

US 8,929,411 B1

QUANTUM DOT DETECTION

This application is a divisional of application Ser. No. 13/226,750, filed Sep. 7, 2011.

BACKGROUND INFORMATION

1. Field

The present disclosure relates generally to testing a surface of an object. More specifically, the disclosure relates to testing a surface to generate data. Even more specifically, the disclosure relates to a method, system, and apparatus for generating images using wavelengths of light generated by quantum dots.

2. Background

Inconsistencies may develop in a surface of an object. An inconsistency is an undesired condition in the material. For example, wear, corrosion, or another inconsistency may develop in a metallic surface of an object. The inconsistency is an undesired condition, because a material having an inconsistency in the surface may not perform as well as a material not having the inconsistency. For example, a metallic surface that has corrosion may not support as much weight as a metallic surface that does not have corrosion.

Non-destructive inspection may be used in testing a surface. For example, the surface of an aircraft body may be inspected to determine whether an inconsistency has developed in the surface. An inspection is non-destructive when the test does not destroy or alter a portion of the object. For example, a surface may be inspected using a camera for corrosion.

The surface to be tested may be larger than the field of view of the measurement tool used to perform the inspection. For example, a camera may only be capable of inspecting a portion of the surface to be tested at a given time. In such an illustrative example, the tool may be moved by an operator from portion to portion of the surface until the desired area of the surface has been tested.

The operator may disable the tool after each portion of the surface is tested. For example, the operator may disable the tool for safety or other reasons, such as when the tool generates particles that may be undesirable to contact a human being. In one illustrative example, the tool may generate an x-ray beam as part of the inspection. In such an illustrative example, the operator disables the tool after a portion of the surface is inspected using the x-ray beam so that the x-ray beam does not contact the human operator.

Currently available methods for testing a surface for undesired inconsistencies, such as corrosion, may not be as accurate as desired. For example, visual inspection of the surface may not provide the data needed to quantify the amount of corrosion as well as desired. As another example, currently-available methods for testing a surface for corrosion may be unable to provide the data needed to detect corrosion as early as desired.

Therefore, it would be advantageous to have a method and apparatus that takes into account at least some of the issues discussed above, as well as possibly other issues.

SUMMARY

In one advantageous embodiment, an apparatus comprises a laser system and a light sensor system. The laser system is associated with a housing and configured to generate a first laser beam and direct the first laser beam toward a surface of an object in which the surface has a plurality of quantum dots. The first laser beam is configured to cause the plurality of quantum dots to generate light. The laser system is further configured to generate a second laser beam and direct the second laser beam toward the light generated by the plurality of quantum dots. The second laser beam is configured to amplify a portion of the light generated by the plurality of quantum dots. The light sensor system is associated with the housing and configured to detect the portion of the light to form data.

In another advantageous embodiment, a system includes a number of tracks, a support structure, a quantum dot detection system, a connection system, and a controller. The number of tracks is configured for placement along a path. The support structure is configured to move on the number of tracks. The quantum dot detection system is moveably connected to the support structure. The quantum dot detection system is configured to identify a presence of a plurality of quantum dots in a portion of a surface of an object and is configured to move along a first axis and a second axis through the support structure. The first axis is substantially perpendicular to the second axis. The connection system is configured to removably connect the number of tracks to the object using a vacuum applied to the surface of the object. The controller is configured to activate and deactivate the quantum dot detection system based on an amount of vacuum applied to the surface of the object.

In yet another advantageous embodiment, a method for generating data using a number of wavelengths of light is provided. A first laser beam is directed toward a surface of an object in which the surface has a plurality of quantum dots. The first laser beam is configured to cause the plurality of quantum dots to generate light. A second laser beam is directed toward the light generated by the plurality of quantum dots. The second laser beam is configured to amplify a portion of the light generated by the plurality of quantum dots. A subset of the number of wavelengths of the light is identified to form data using a light sensor system.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives, and advantages thereof will best be understood by reference to the following detailed description of an advantageous embodiment of the present disclosure when read in conjunction with the accompanying drawings, wherein:

FIG. 10 is an illustration of a data processing system in accordance with an advantageous embodiment.

DETAILED DESCRIPTION

Figure 1:
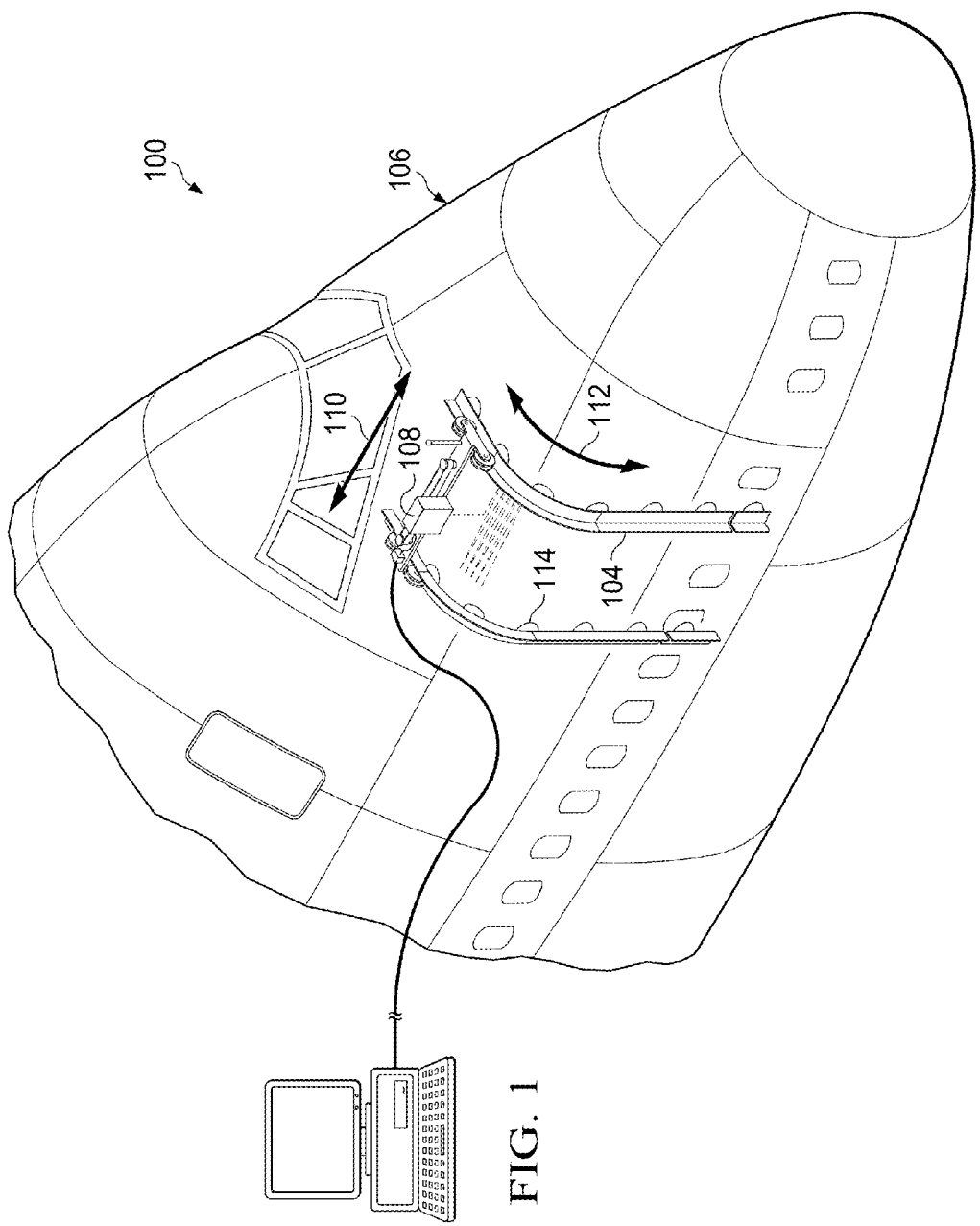
FIG. 1 is an illustration of an aircraft in accordance with an advantageous embodiment.

With reference now to the figures, and with particular reference to FIG. 1, an illustration of an aircraft is depicted in accordance with an advantageous embodiment. Aircraft 100 is an example of an object for which a plurality of quantum dots is to be identified, such as plurality of quantum dots 210 in FIG. 2.

In this advantageous embodiment, number of tracks 104 is positioned on the surface of fuselage 106. Number of tracks 104 is positioned along a desired path for identifying the presence of quantum dots. A connection system removably attaches number of tracks 104 to fuselage 106. The connection system removes air and generates a vacuum in a volume bound by suction cups attached to the tracks and the surface of fuselage 106. For example, suction cup 114 attaches a track in number of tracks 104 to fuselage 106 when the air between suction cup 114 and fuselage 106 is removed.

Figure 2:
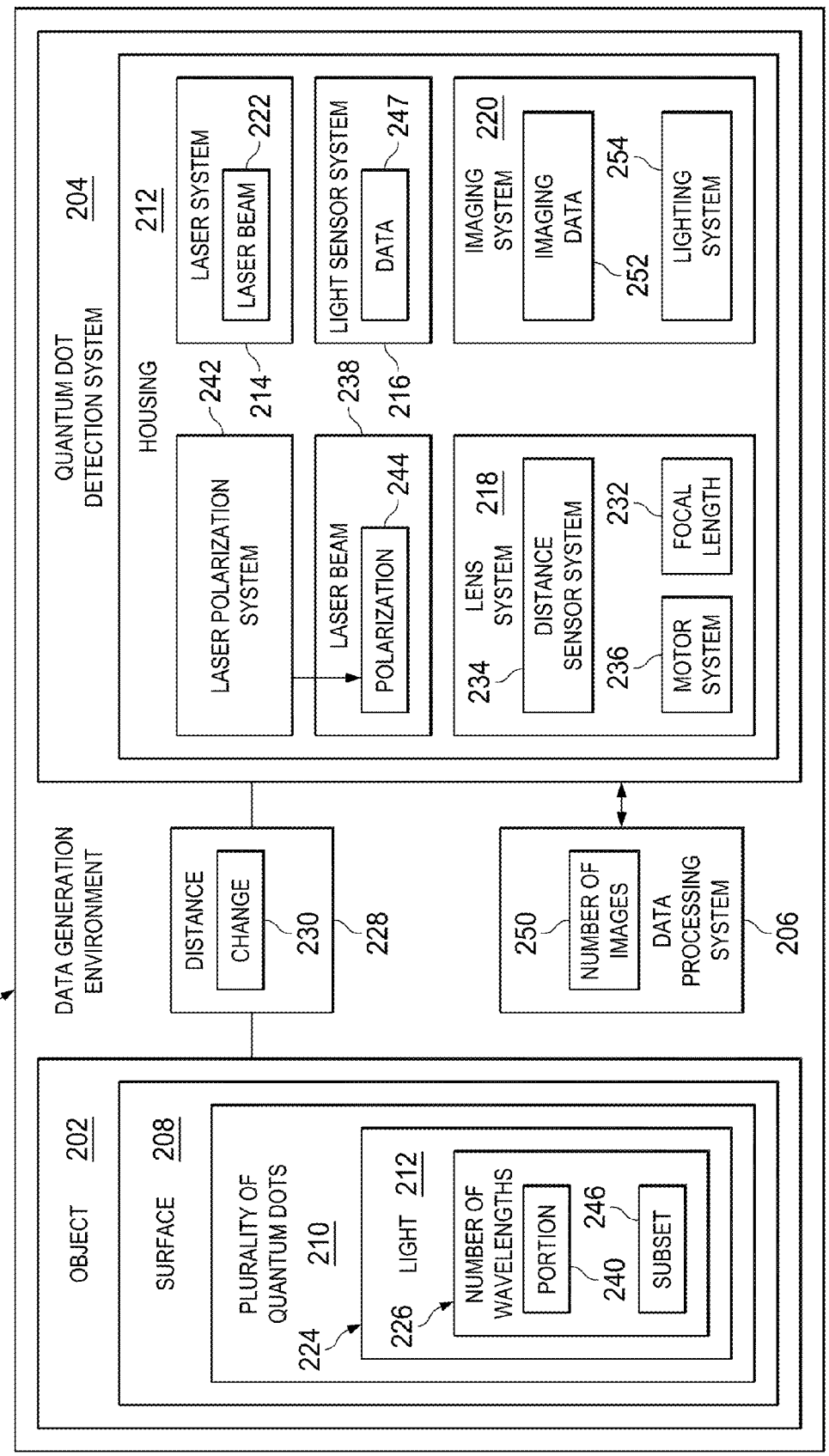
FIG. 2 is an illustration of a block diagram of a data generation environment in accordance with an advantageous embodiment.

A quantum dot detection system, such as quantum dot detection system 204 in FIG. 2, located at least partially inside light reduction structure 108, may be moved along the tracks using a motor system in direction 112. Additionally, the quantum dot detection system and/or the light reduction structure may move along a support structure that extends between the tracks in direction 110.

Once positioned, the quantum dot detection system generates a laser beam that causes a plurality of quantum dots on the surface of fuselage 106 to generate light. The quantum dot detection system then generates a second laser beam that amplifies a subset of the number of wavelengths of light generated by the plurality of quantum dots. A sensor system then identifies the presence of the subset of the number of wavelengths of light as the presence of quantum dots on the surface of fuselage 106. The quantum dot detection system and/or light reduction structure 108 may be moved using motor systems and without human intervention.

The different advantageous embodiments recognize and take into account a number of different considerations. For example, painted surfaces may be difficult to identify, because the surface underneath the paint may not be visually inspected. For example, a painted metallic surface may experience corrosion that is difficult to detect visually, because the paint covers the corrosion on the metallic surface.

The different advantageous embodiments also recognize and take into account that particles may be present in the paint to aid the identification of inconsistencies in the surface beneath the paint. For example, the paint may include quantum dots. Quantum dots are particles that generate light when light having particular wavelengths contacts the quantum dots.

The different advantageous embodiments also recognize and take into account that disabling and moving a tool to perform inspection of multiple portions of a surface may be time and labor-intensive. The different advantageous embodiments allow an operator to set up tracks that removably attach to the surface of the object and position the tool along the tracks such that the tool may be moved using motor systems. The tool may then be used to identify inconsistencies in the desired portion of the surface of the object without the human operator disabling, moving, and re-enabling the tool.

The different advantageous embodiments also recognize and take into account that the inspection process may generate particles that are undesirable to be in contact with a human operator. For example, a human operator may experience undesirable health results from a laser beam contacting the human operator. The different advantageous embodiments disable the tool when the tool or a component of the track system is no longer in contact with the surface of the object.

Thus, the different advantageous embodiments provide an apparatus and method for generating data using a number of wavelengths of light. In one advantageous embodiment, an apparatus comprises a laser system and a light sensor system. The laser system is associated with a housing and configured to generate a first laser beam and direct the first laser beam toward a surface of an object in which the surface has a plurality of quantum dots. The first laser beam is configured to cause the plurality of quantum dots to generate light. The laser system is further configured to generate a second laser beam and direct the second laser beam toward the light generated by the plurality of quantum dots. The second laser beam is configured to amplify a portion of the light generated by the plurality of quantum dots. The light sensor system associated with the housing is configured to detect the portion of the light to form data.

Turning now to FIG. 2, an illustration of a block diagram of a data generation environment is depicted in accordance with an advantageous embodiment. Data generation environment 200 is an example of an environment in which advantageous embodiments may be implemented.

Data generation environment 200 includes object 202, quantum dot detection system 204, and data processing system 206. Object 202 is an object having at least one surface 208. Surface 208 is an area on object 202 to be inspected for a number of inconsistencies. As used herein, "a number of" items means one or more items. For example, a number of inconsistencies means one or more inconsistencies.

In these advantageous embodiments, surface 208 is an area of object 202 that includes plurality of quantum dots 210. Plurality of quantum dots 210 is composed of particles that fluoresce when contacted by light of a particular set of wavelengths. In other words, plurality of quantum dots 210 generates light when contacted by light having a particular set of wavelengths. In this advantageous embodiment, surface 208 is a metallic surface that is painted with paint that includes plurality of quantum dots 210.

Quantum dots are particles that generate light when light having particular wavelengths contacts the quantum dots. More specifically, a quantum dot is a portion of matter having excitons that are confined in all three spatial dimensions. Further, quantum dots are nanoscale semiconductor-type crystals that fluoresce when the quantum dots have been excited by being contacted by particular wavelengths of light. The wavelength of the light that fluoresces from the quantum dots varies based on quantum dot band gap and the size of the quantum dots.

Quantum dot detection system 204 is used to identify whether an inconsistency has developed in surface 208 of object 202. For example, quantum dot detection system 204 may be used to identify whether corrosion has occurred in surface 208. Quantum dot detection system 204 includes housing 212. Laser system 214, light sensor system 216, and lens system 218 are associated with housing 212 in these advantageous embodiments.

A first component may considered to be associated with a second component by being secured to the second component, bonded to the second component, fastened to the second component, and/or connected to the second component in some other suitable manner. The first component may also be considered to be associated with the second component by being formed as part of and/or an extension of the second component.

Laser system 214 generates laser beam 222. Laser means Light Amplification by Stimulated Emission of Radiation in these illustrative examples. Laser beam 222 is a beam of laser light. In this advantageous embodiment, laser system 214 generates laser beam 222 and directs laser beam 222 toward surface 208 of object 202. Laser beam 222 travels through lens system 218 before contacting surface 208.

Lens system 218 includes a lens that focuses laser beam 222 on surface 208. In the event that distance 228 between quantum dot detection system 204 and surface 208 experiences change 230, lens system 218 changes focal length 232 of lens system 218 to maintain focus of laser beam 222 on surface 208. In this advantageous embodiment, lens system 218 identifies distance 228 using distance sensor system 234. For example, distance sensor system 234 may be an automatic standoff system. Further, in this advantageous embodiment, lens system 218 uses motor system 236 to modify focal length 232 of lens system 218. In some advantageous embodiments, lens system 218 may include a single lens. However, in other advantageous embodiments, lens system 218 includes multiple lenses through which laser beam 222 travels before contacting surface 208.

Laser beam 222 generated by laser system 214 includes light of a wavelength that causes plurality of quantum dots 210 to generate light 224 when laser beam 222 contacts plurality of quantum dots 210 in surface 208. Light 224 is of number of wavelengths 226 in this advantageous embodiment. At least some of number of wavelengths 226 of light 224 may be, for example, without limitation, visible light, infrared, or another suitable type of light.

Once laser beam 222 has contacted plurality of quantum dots 210 and caused plurality of quantum dots 210 to generate light 224, laser system 214 generates laser beam 238. In some advantageous embodiments, laser system 214 ceases generating laser beam 222 prior to generating laser beam 238. In other advantageous embodiments, laser system 214 continues to generate laser beam 222 while generating laser beam 238. In yet other advantageous embodiments, laser system 214 uses optics and/or mirror systems to split a single laser beam into laser beam 222 and laser beam 238.

Laser system 214 directs laser beam 238 toward light 224 generated by plurality of quantum dots 210. In these illustrative examples, laser beam 238 is reflected using a number of mirrors and then travels through lens system 218 prior to contacting light 224. Lens system 218 may also focus laser beam 238 on light 224 and/or plurality of quantum dots 210 on surface 208.

Laser beam 238 is of a wavelength that amplifies portion 240 of number of wavelengths 226 of light 224. In some advantageous embodiments, light in laser beam 238 is of a wavelength that adds to the intensity of portion 240 of light 224. In other advantageous embodiments, laser beam 238 is of a wavelength that reduces the fluorescent state by stimulated emission of portion 240 of number of wavelengths 226 of light 224. In other words, laser beam 238 is of a wavelength that causes plurality of quantum dots 210 to return to a non-excited state. Thus, portion 240 of number of wavelengths 226 of light 224 remains after laser beam 238 contacts plurality of quantum dots 210. Laser beam 238 may be used to generate sub-diffraction images.

In the event that surface 208 is reflective, laser beam 238 may be at least partially reflected when contacting surface 208. In such an advantageous embodiment, an operator may activate laser polarization system 242. Laser polarization system 242 is a device that modifies polarization 244 of laser beam 238 while laser beam 238 is traveling toward light 224. For example, laser polarization system 242 may use a number of polarizing filters to modify polarization 244 of laser beam 238 by about half of a wave.

Quantum dot detection system 204 then activates light sensor system 216. Light sensor system 216 includes a number of sensors that identify subset 246 of number of wavelengths 226 of light 224. In other words, light sensor system 216 identifies the presence of subset 246 of number of wavelengths 226 of light 224 being generated by plurality of quantum dots 210 on surface 208. Light sensor system 216 then generates data 247 that indicates whether subset 246 was identified.

Quantum dot detection system 204 then sends data 247 to data processing system 206. Data processing system 206 receives data 247 and generates number of images 250. Number of images 250 is a collection of images generated that depict light 224 generated by plurality of quantum dots 210 on surface 208. Each image in number of images 250 may be generated while quantum dot detection system 204 is located at a particular position on surface 208. In other words, data processing system 206 may combine data 247 generated for different portions of surface 208 to form number of images 250.

The illustration of data generation environment 200 in FIG. 2 is not meant to imply physical or architectural limitations to the manner in which different advantageous embodiments may be implemented. Other components in addition to and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

For example, in some advantageous embodiments, quantum dot detection system 204 also includes imaging system 220 associated with housing 212. Imaging system 220 generates imaging data 252. Imaging data 252 includes image information generated using visible light. Imaging system 220 includes a camera system in these advantageous embodiments. In some advantageous embodiments, imaging system 220 further includes lighting system 254. Lighting system 254 may use light to illuminate surface 208 so that imaging system 220 may generate imaging data 252.

The different components shown in FIG. 1 and FIGS. 4-6 may be combined with components in FIG. 2, used with components in FIG. 2, or a combination of the two. Additionally, some of the components in FIG. 1 and FIGS. 4-6 may be illustrative examples of how components shown in block form in FIG. 2 can be implemented as physical structures.

Figure 3:
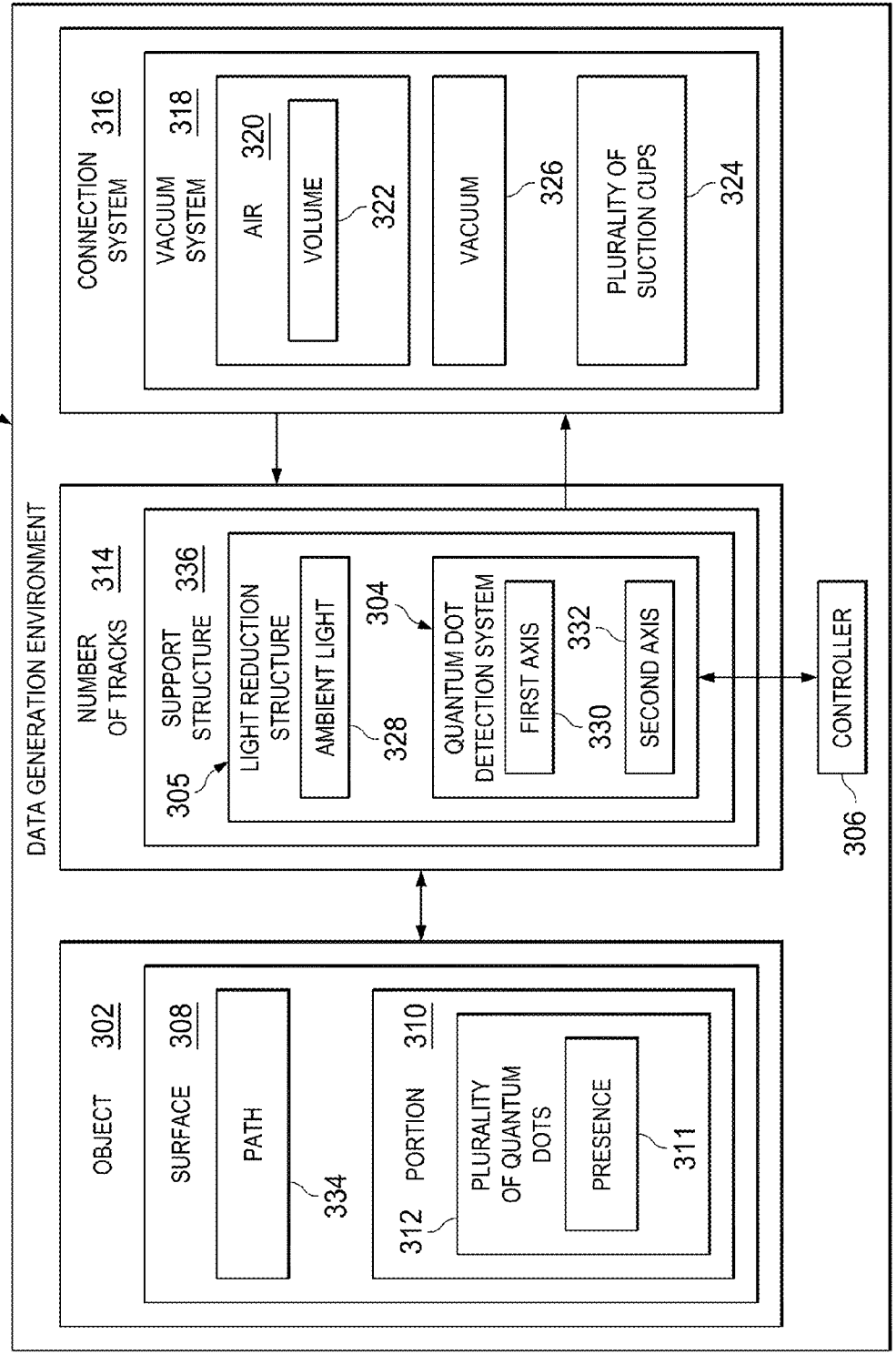
FIG. 3 is an illustration of a data generation environment in accordance with an advantageous embodiment.

Looking now to FIG. 3, an additional illustration of a data generation environment is depicted in accordance with an advantageous embodiment. Data generation environment 300 is an example implementation of data generation environment 200 in FIG. 2.

Data generation environment 300 includes object 302, quantum dot detection system 304, and controller 306 in this advantageous embodiment. Object 302 is an example of object 202, quantum dot detection system 304 is an example of quantum dot detection system 204, and controller 306 is an example of data processing system 206 in FIG. 2.

In this advantageous embodiment, quantum dot detection system 304 is used to identify inconsistencies in portion 310 of surface 308 of object 302. In one advantageous embodiment, quantum dot detection system 304 identifies presence 311 of plurality of quantum dots 312. Portion 310 is a desired area on surface 308. For example, portion 310 may be a particular area on the outward facing side of a fuselage of an aircraft. Portion 310 of surface 308 includes plurality of quantum dots 312. Plurality of quantum dots 312 is an example of plurality of quantum dots 210 in FIG. 2.

Quantum dot detection system 304 is associated with light reduction structure 305 in this advantageous embodiment. Light reduction structure 305 is an object that substantially blocks ambient light 328 from contacting portion 310 and/or quantum dot detection system 304. Ambient light 328 is the light from the environment surrounding surface 308 that contacts surface 308. In other words, ambient light 328 is the light that contacts surface 308 that is not generated by quantum dot detection system 304.

In these illustrative examples, quantum dot detection system 304 travels within light reduction structure 305 along first axis 330 and second axis 332. First axis 330 and second axis 332 may be substantially perpendicular. In other words, quantum dot detection system 304 may move in two directions within light reduction structure 305. For example, a motor system may cause quantum dot detection system 304 to move within light reduction structure 305.

In these illustrative examples, number of tracks 314 is removably connected to object 302 along path 334. For example, number of tracks 314 may be connected to object 302 using connection system 316. Connection system 316 includes vacuum system 318 in these advantageous embodiments. Vacuum system 318 removably attaches number of tracks 314 to object 302 by removing air 320 from volume 322 bound by surface 308 of object 302 and plurality of suction cups 324. Plurality of suction cups 324 is objects that attach number of tracks 314 to surface 308 of object 302 when air 320 is removed from volume 322 and vacuum 326 is generated. When vacuum 326 is no longer present and air 320 has returned to volume 322, plurality of suction cups 324 ceases attaching number of tracks 314 to object 302.

Support structure 336 is a structure that extends between number of tracks 314 such that light reduction structure 305 may be moved along support structure 336. Since quantum dot detection system 304 is at least partially contained in light reduction structure 305, quantum dot detection system 304 may also move with light reduction structure 305 along support structure 336 in addition to moving within light reduction structure 305 along first axis 330 and second axis 332.

Thus, number of tracks 314 may be positioned along path 334 that is desired to identify inconsistencies in portion 310 of surface 308. Light reduction structure 305 may then move along support structure 336, and support structure 336 may move along number of tracks 314 to position light reduction structure 305 at the first location on surface 308 that is desired. Quantum dot detection system 304 may then generate data and send the data to controller 306 for a particular area of surface 308. Quantum dot detection system 304 may then be moved along first axis 330 and/or second axis 332, and data may be generated and sent to controller 306 again without moving light reduction structure 305.

Quantum dot detection system 304 may repeat generating data and moving within light reduction structure 305 until quantum dot detection system 304 has generated data for each location on surface 308 that is covered by light reduction structure 305. Light reduction structure 305 may then be moved along support structure 336 and/or number of tracks 314 to position light reduction structure 305 and quantum dot detection system 304 in another location on surface 308. Quantum dot detection system 304 and/or light reduction structure 305 may be moved and data generated by quantum dot detection system 304 until data has been generated for all of portion 310 of surface 308 that is desired. Controller 306 may then generate a number of images using the data, such as number of images 250 in FIG. 2.

Figure 4:
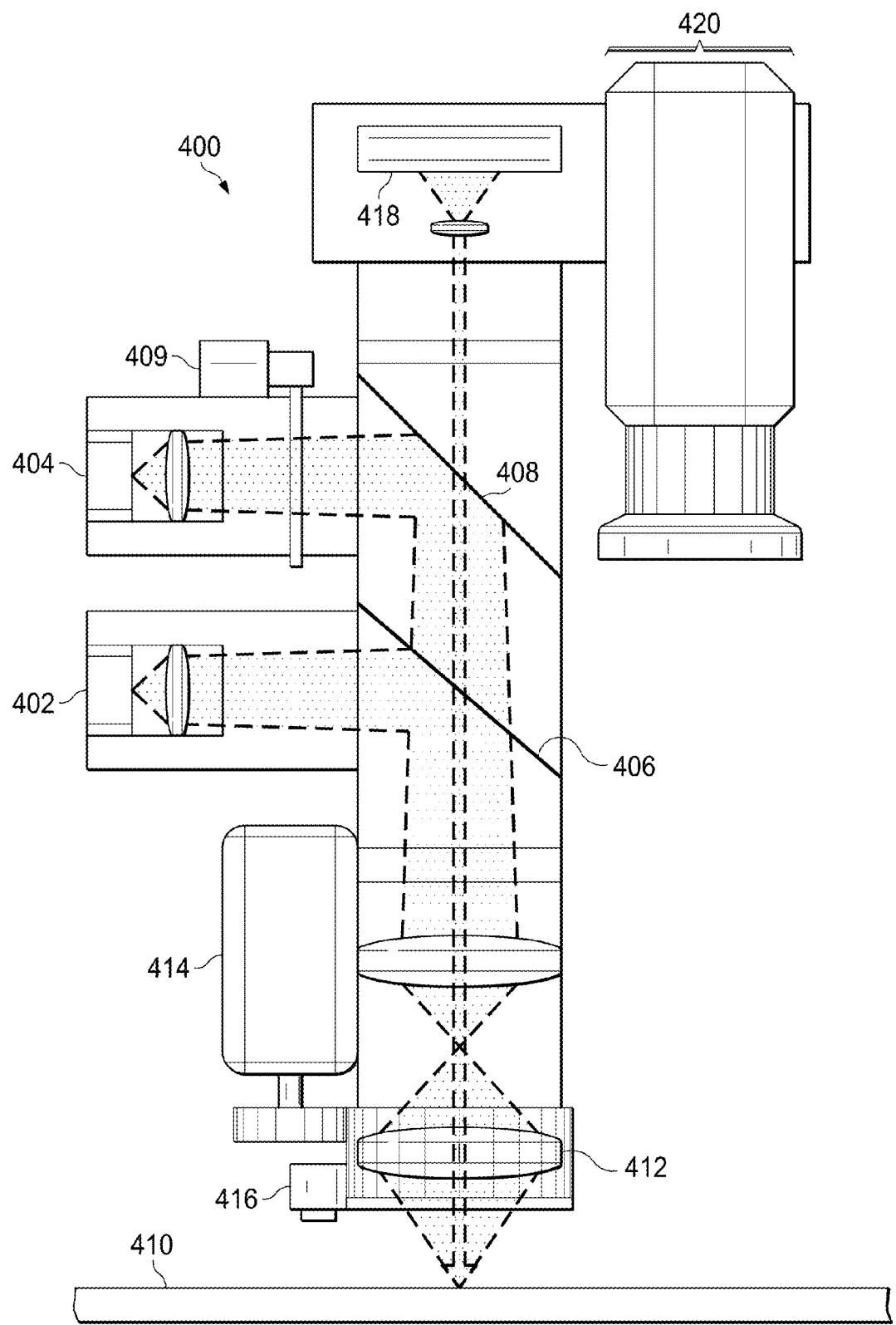
FIG. 4 is an illustration of a quantum dot detection system in accordance with an advantageous embodiment.

Looking now to FIG. 4, an illustration of a quantum dot detection system is depicted in accordance with an advantageous embodiment. Quantum dot detection system 400 is an example implementation of quantum dot detection system 204 in FIG. 2.

Quantum dot detection system 400 includes a laser system, such as laser system 214 in FIG. 2. In this advantageous embodiment, quantum dot detection system 400 includes two laser beam generators, laser beam generator 402 and laser beam generator 404. Laser beam generator 402 generates a laser beam, such as laser beam 222 in FIG. 2. Likewise, laser beam generator 404 generates a laser beam, such as laser beam 238 in FIG. 2. Mirror 406 redirects the laser beam generated by laser beam generator 402 toward surface 410. In some advantageous embodiments, mirror 406 is a beam splitter. Likewise, mirror 408 redirects the laser beam generated by laser beam generator 402 toward surface 410. Laser polarization system 409 is an example implementation of laser polarization system 242 in FIG. 2. A motor associated with laser polarization system 409 may be activated to adjust a polarization filter associated with laser polarization system 409 such that the polarization of the laser beam generated by laser beam generator 404 is modified.

The laser beams travel through a lens system before contacting surface 410. Lens 412 and motor 414 are an example implementation of lens system 218 in FIG. 2. The lens system further includes distance sensor 416. Distance sensor 416 is an example implementation of distance sensor system 234 in FIG. 2. Distance sensor 416 identifies a change in distance between lens 412 and surface 410. When a change in distance occurs, the lens system modifies the focal length of lens 412 using motor 414 to maintain focus for the laser beams traveling through lens 412.

When the laser beam generated by laser beam generator 404 contacts the light generated by the plurality of quantum dots, light sensor system 418 is activated. Light sensor system 418 is an example implementation of light sensor system 216 in FIG. 2. A subset of the number of wavelengths of light generated by the quantum dots are received by light sensor system 418, and light sensor system 418 identifies that the subset of the number of wavelengths is present in data generated by light sensor system 418.

In some advantageous embodiments, quantum dot detection system 400 also includes camera system 420. Camera system 420 generates images using wavelengths of light in the visible portion of the electromagnetic spectrum. Camera system 420 may also include a lighting system that illuminates surface 410 when camera system 420 is generating image data.

Figure 5:
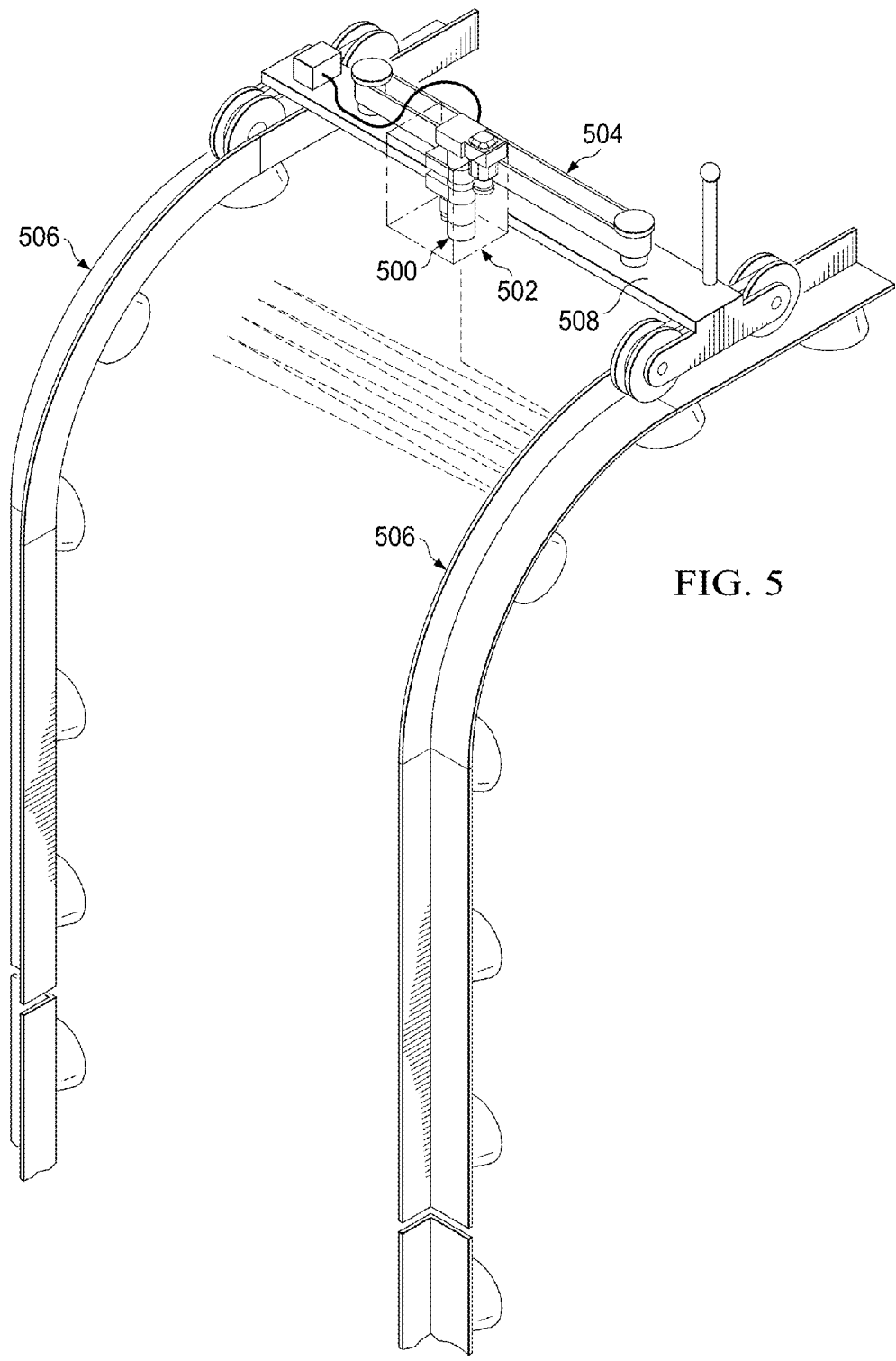
FIG. 5 is an illustration of a quantum dot detection system in accordance with an advantageous embodiment.

Turning now to FIG. 5, an additional illustration of a quantum dot detection system is depicted in accordance with an advantageous embodiment. Quantum dot detection system 500 is an example implementation of quantum dot detection system 204 in FIG. 2. Quantum dot detection system 500 is depicted at least partially inside light reduction structure 502 in this advantageous embodiment. Light reduction structure 502 is an example implementation of light reduction structure 305 in FIG. 3.

In this illustrative example, quantum dot detection system 500 moves within light reduction structure 502, and light reduction structure 502 moves along support structure 504 using a motor system. Support structure 504 may also be moved along number of tracks 506 using motor system 508.

Figure 6:
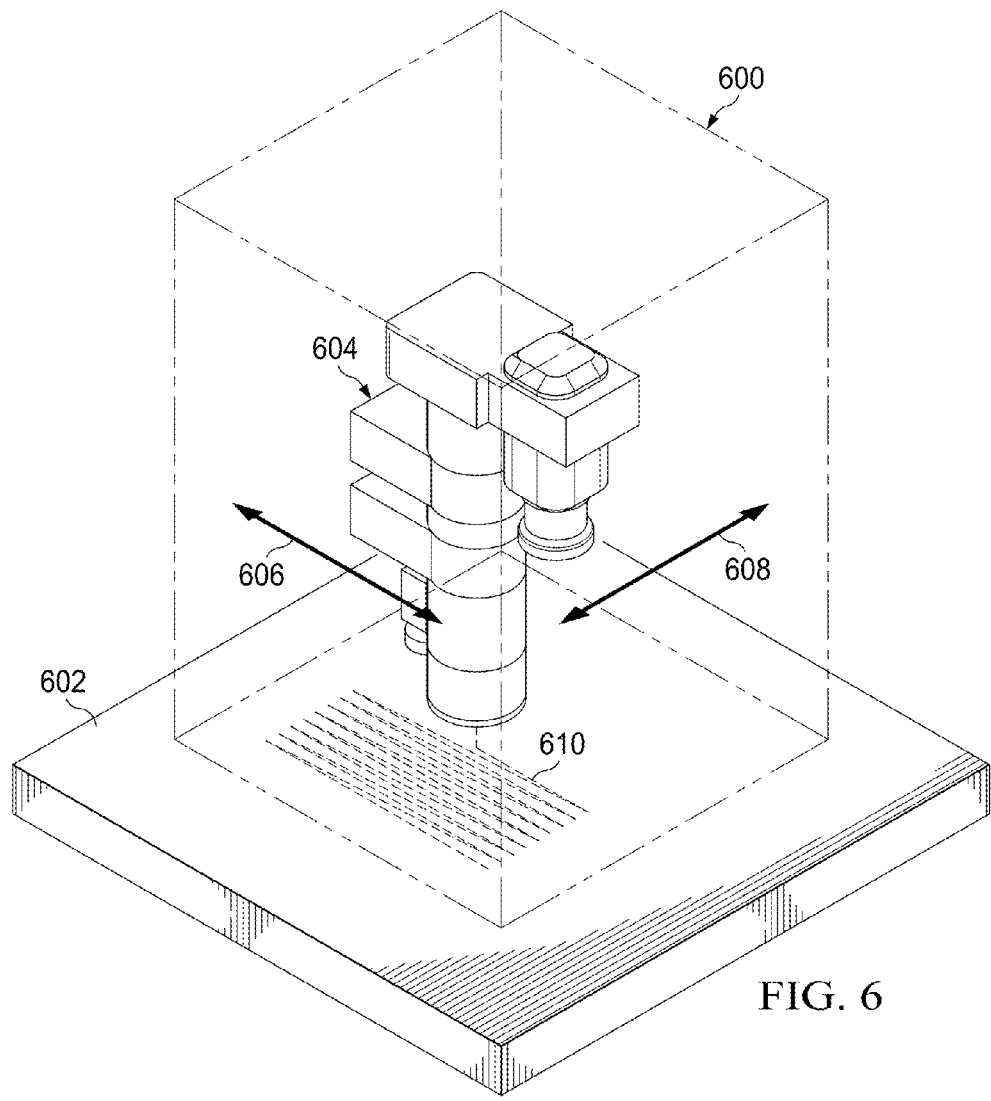
FIG. 6 is an illustration of a light reduction structure in accordance with an advantageous embodiment.

Looking now to FIG. 6, an illustration of a light reduction structure is depicted in accordance with an advantageous embodiment. Light reduction structure 600 is an example implementation of light reduction structure 305 in FIG. 3.

In this advantageous embodiment, quantum dot detection system 604 is configured to identify inconsistencies in surface 602 by moving in direction 606 and/or direction 608 within light reduction structure 600. In the illustrative examples, quantum dot detection system 604 may move within light reduction structure 600 without moving light reduction structure 600. As an illustrative example, quantum dot detection system 604 may move in pattern 610 and generate data at a particular number of locations within pattern 610.

The illustration of quantum dot detection system 604 is not intended to limit the manner in which other advantageous embodiments may be implemented. The illustrations in FIGS. 4-6 are meant merely as examples of physical implementations for quantum dot detection system 204 in FIG. 2.

Figure 7:
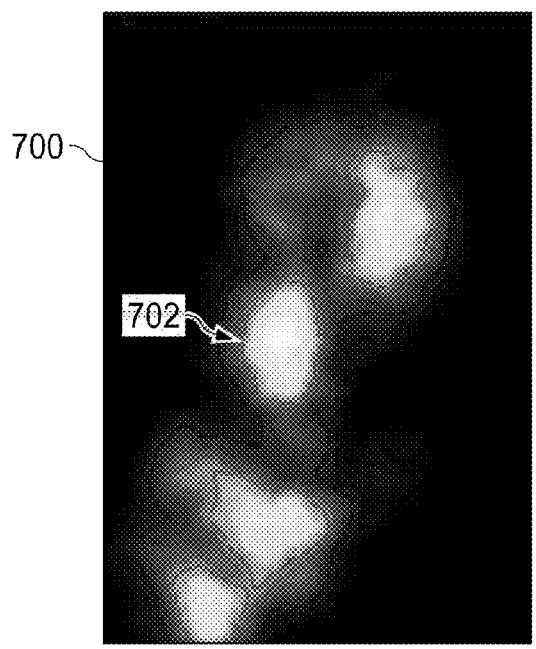
FIG. 7 is an illustration of an image generated by a data processing system in accordance with an advantageous embodiment.

Looking now to FIG. 7, an illustration of an image generated by a data processing system is depicted in accordance with an advantageous embodiment. Image 700 is an example of an image in number of images 250 that may be generated by data processing system 206 in FIG. 2. In this advantageous embodiment, area 702 depicts the presence of quantum dots.

Figure 8:
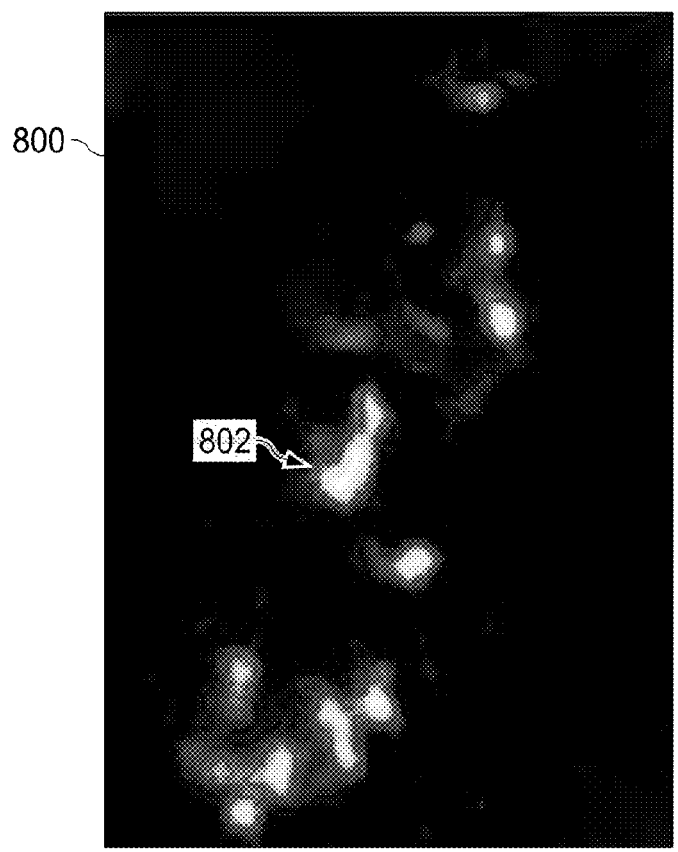
FIG. 8 is an illustration of another image generated by a data processing system in accordance with an advantageous embodiment.

With reference now to FIG. 8, an illustration of another image generated by a data processing system is depicted in accordance with an advantageous embodiment. Image 800 also depicts the presence of quantum dots in area 802. However, the intensity of the light generated by the quantum dots is lower than the intensity in area 702 in FIG. 7. Thus, an inconsistency may have developed in area 802 of the surface being inspected when image 800 was generated.

Figure 9:
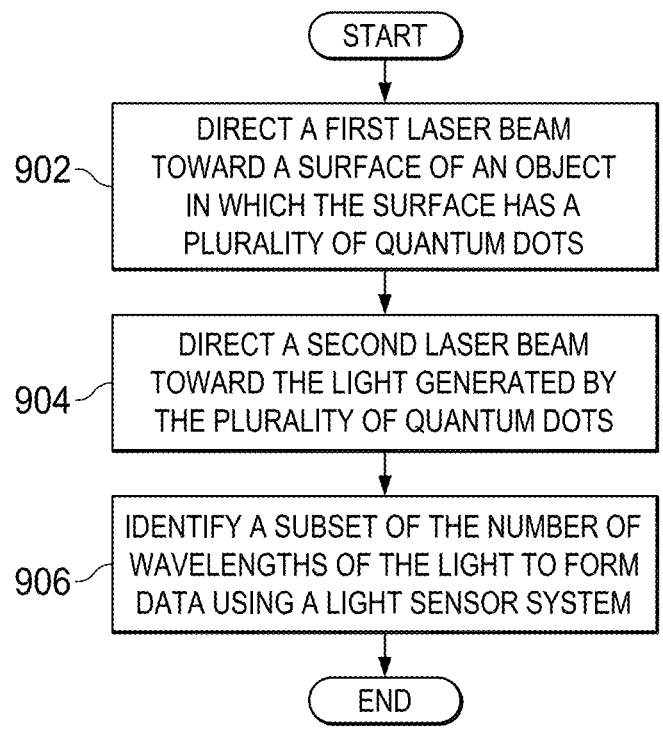
FIG. 9 is an illustration of a flowchart of a process for generating data using a number of wavelengths of light in accordance with an advantageous embodiment.

Looking now to FIG. 9, an illustration of a flowchart of a process for generating data using a number of wavelengths of light is depicted in accordance with an advantageous embodiment. The process in FIG. 9 may be performed by quantum dot detection system 204 in FIG. 2.

The process begins by directing a first laser beam toward a surface of an object in which the surface has a plurality of quantum dots (operation 902). The first laser beam causes the plurality of quantum dots to generate light when the first laser beam contacts the plurality of quantum dots. The process then directs a second laser beam toward the light generated by the plurality of quantum dots (operation 904). The second laser beam amplifies a portion of the light generated by the plurality of quantum dots. In some advantageous embodiments, the portion of the light is a number of wavelengths of light.

The process then identifies a subset of the number of wavelengths of the light to form data using a light sensor system (operation 906). The light sensor system may be light sensor system 216 in FIG. 2. The subset of the number of wavelengths may be a collection of wavelengths to which the light sensor system is configured to receive. For example, the light sensor system may generate data indicating that the quantum dots are present at the location being inspected when the subset of the number of wavelengths is received by the light sensor system. The process terminates thereafter.

Turning now to FIG. 10, an illustration of a data processing system is depicted in accordance with an advantageous embodiment. Data processing system 1000 is an example of data processing system 206 in FIG. 2.

In this illustrative example, data processing system 1000 includes communications fabric 1002, which provides communications between processor unit 1004, memory 1006, persistent storage 1008, communications unit 1010, input/output (I/O) unit 1012, and display 1014.

Processor unit 1004 serves to execute instructions for software that may be loaded into memory 1006. Processor unit 1004 may be a number of processors, a multi-processor core, or some other type of processor, depending on the particular implementation. A number, as used herein with reference to an item, means one or more items. Further, processor unit 1004 may be implemented using a number of heterogeneous processor systems in which a main processor is present with secondary processors on a single chip. As another illustrative example, processor unit 1004 may be a symmetric multi-processor system containing multiple processors of the same type.

Memory 1006 and persistent storage 1008 are examples of storage devices 1016. A storage device is any piece of hardware that is capable of storing information, such as, for example, without limitation, data, program code in functional form, and/or other suitable information either on a temporary basis and/or a permanent basis. Storage devices 1016 may also be referred to as computer readable storage devices in these examples. Memory 1006, in these examples, may be, for example, a random access memory or any other suitable volatile or non-volatile storage device. Persistent storage 1008 may take various forms, depending on the particular implementation.

For example, persistent storage 1008 may contain one or more components or devices. For example, persistent storage 1008 may be a hard drive, a flash memory, a rewritable optical disk, a rewritable magnetic tape, or some combination of the above. The media used by persistent storage 1008 also may be removable. For example, a removable hard drive may be used for persistent storage 1008.

Communications unit 1010, in these examples, provides for communications with other data processing systems or devices. In these examples, communications unit 1010 is a network interface card. Communications unit 1010 may provide communications through the use of either or both physical and wireless communications links.

Input/output unit 1012 allows for input and output of data with other devices that may be connected to data processing system 1000. For example, input/output unit 1012 may provide a connection for user input through a keyboard, a mouse, and/or some other suitable input device. Further, input/output unit 1012 may send output to a printer. Display 1014 provides a mechanism to display information to a user.

Instructions for the operating system, applications, and/or programs may be located in storage devices 1016, which are in communication with processor unit 1004 through communications fabric 1002. In these illustrative examples, the instructions are in a functional form on persistent storage 1008. These instructions may be loaded into memory 1006 for execution by processor unit 1004. The processes of the different embodiments may be performed by processor unit 1004 using computer implemented instructions, which may be located in a memory, such as memory 1006.

These instructions are referred to as program code, computer usable program code, or computer readable program code that may be read and executed by a processor in processor unit 1004. The program code in the different embodiments may be embodied on different physical or computer readable storage media, such as memory 1006 or persistent storage 1008.

Program code 1018 is located in a functional form on computer readable media 1020 that is selectively removable and may be loaded onto or transferred to data processing system 1000 for execution by processor unit 1004. Program code 1018 and computer readable media 1020 form computer program product 1022 in these examples. In one example, computer readable media 1020 may be computer readable storage media 1024 or computer readable signal media 1026. Computer readable storage media 1024 may include, for example, an optical or magnetic disk that is inserted or placed into a drive or other device that is part of persistent storage 1008 for transfer onto a storage device, such as a hard drive, that is part of persistent storage 1008. Computer readable storage media 1024 also may take the form of a persistent storage, such as a hard drive, a thumb drive, or a flash memory, that is connected to data processing system 1000. In some instances, computer readable storage media 1024 may not be removable from data processing system 1000. In these illustrative examples, computer readable storage media 1024 is a non-transitory computer readable storage medium.

Alternatively, program code 1018 may be transferred to data processing system 1000 using computer readable signal media 1026. Computer readable signal media 1026 may be, for example, a propagated data signal containing program code 1018. For example, computer readable signal media 1026 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some advantageous embodiments, program code 1018 may be downloaded over a network to persistent storage 1008 from another device or data processing system through computer readable signal media 1026 for use within data processing system 1000. For instance, program code stored in a computer readable storage medium in a server data processing system may be downloaded over a network from the server to data processing system 1000. The data processing system providing program code 1018 may be a server computer, a client computer, or some other device capable of storing and transmitting program code 1018.

The different components illustrated for data processing system 1000 are not meant to provide architectural limitations to the manner in which different embodiments may be implemented. The different advantageous embodiments may be implemented in a data processing system including components in addition to or in place of those illustrated for data processing system 1000. Other components shown in FIG. 10 can be varied from the illustrative examples shown. The different embodiments may be implemented using any hardware device or system capable of running program code. As one example, the data processing system may include organic components integrated with inorganic components and/or may be comprised entirely of organic components excluding a human being. For example, a storage device may be comprised of an organic semiconductor.

In another illustrative example, processor unit 1004 may take the form of a hardware unit that has circuits that are manufactured or configured for a particular use. This type of hardware may perform operations without needing program code to be loaded into a memory from a storage device to be configured to perform the operations.

For example, when processor unit 1004 takes the form of a hardware unit, processor unit 1004 may be a circuit system, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, programmable array logic, a field programmable logic array, a field programmable gate array, and other suitable hardware devices. With this type of implementation, program code 1018 may be omitted, because the processes for the different embodiments are implemented in a hardware unit.

In still another illustrative example, processor unit 1004 may be implemented using a combination of processors found in computers and hardware units. Processor unit 1004 may have a number of hardware units and a number of processors that are configured to run program code 1018. With this depicted example, some of the processes may be implemented in the number of hardware units, while other processes may be implemented in the number of processors.

As another example, a storage device in data processing system 1000 is any hardware apparatus that may store data. Memory 1006, persistent storage 1008, and computer readable media 1020 are examples of storage devices in a tangible form.

In another example, a bus system may be used to implement communications fabric 1002 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 1006, or a cache, such as found in an interface and memory controller hub that may be present in communications fabric 1002.

In these illustrative examples, data processing system 1000 may receive data using communications unit 1010 from a quantum dot detection system, such as quantum dot detection system 204 in FIG. 2. Data processing system 1000 may then store the data in storage devices 1016 until data from a particular number of locations on a surface has been received. Then, data processing system 1000 may use processor unit 1004 and program code 1018 to combine data from the different locations to form a number of images. The data may include information about the location of the quantum dot detection system when the data is generated.

The different advantageous embodiments allow an operator to position tracks along a path that includes the portion of a surface that the operator desires to inspect for inconsistencies. Once the tracks are in position, the operator may activate the vacuum system to attach the tracks to the surface until the vacuum is deactivated. The quantum dot detection system and the light reduction structure may then move along a support structure extending between the tracks, as well as along the tracks. Further, the quantum dot detection system may move along two axes within the light reduction structure. Thus, the light reduction structure may remain in a constant position while an area on the surface is inspected by the quantum dot detection system by moving within the light reduction structure. By not repositioning the system after each location on the surface is inspected, the operator reduces the amount of time used to inspect the surface.

Further, the different advantageous embodiments allow an operator to identify inconsistencies in surfaces that are painted or otherwise obscured using quantum dots that are in the paint or obscuring material. The operator may identify that inconsistencies are present when the quantity of quantum dots in a particular area of the surface is below a threshold amount and/or a distribution pattern of the quantum dots differs from the desired pattern.

Thus, the different advantageous embodiments provide an apparatus and method for generating data using a number of wavelengths of light. In one advantageous embodiment, an apparatus comprises a laser system and a light sensor system. The laser system is associated with a housing and configured to generate a first laser beam and direct the first laser beam toward a surface of an object in which the surface has a plurality of quantum dots. The first laser beam is configured to cause the plurality of quantum dots to generate light. The laser system is further configured to generate a second laser beam and direct the second laser beam toward the light generated by the plurality of quantum dots. The second laser beam is configured to amplify a portion of the light generated by the plurality of quantum dots. The light sensor system is associated with the housing and configured to detect the portion of the light to form data.

In another advantageous embodiment, a system includes a number of tracks, a support structure, a quantum dot detection system, a connection system, and a controller. The number of tracks is configured for placement along a path. The support structure is configured to move on the number of tracks. The quantum dot detection system is moveably connected to the support structure. The quantum dot detection system is configured to identify a presence of a plurality of quantum dots in a portion of a surface of an object and is configured to move along a first axis and a second axis through the support structure. The first axis is substantially perpendicular to the second axis. The connection system is configured to removably connect the number of tracks to the object using a vacuum applied to the surface of the object. The controller is configured to activate and deactivate the quantum dot detection system based on an amount of vacuum applied to the surface of the object.

In yet another advantageous embodiment, a method for generating data using a number of wavelengths of light is provided. A first laser beam is directed toward a surface of an object in which the surface has a plurality of quantum dots. The first laser beam is configured to cause the plurality of quantum dots to generate light. A second laser beam is directed toward the light generated by the plurality of quantum dots. The second laser beam is configured to amplify a portion of the light generated by the plurality of quantum dots. The subset of the number of wavelengths of the light is identified to form data using a light sensor system.

The description of the different advantageous embodiments has been presented for purposes of illustration and description and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A system comprising:
    a number of tracks configured for placement along a path;
    a support structure configured to move on the number of tracks;
    a quantum dot detection system moveably connected to the support structure, wherein the quantum dot detection system is configured to identify a presence of a plurality of quantum dots in a portion of a surface of an object and is configured to move along a first axis and a second axis through the support structure, and wherein the first axis is substantially perpendicular to the second axis;
    a connection system configured to removably connect the number of tracks to the object using a vacuum applied to the surface of the object; and
    a controller configured to activate and deactivate the quantum dot detection system based on an amount of the vacuum applied to the surface of the object.

2. The system of claim 1 further comprising:
    a light reduction structure moveably connected to the support structure and configured to move along the first axis through the support structure, wherein the quantum dot detection system is associated with the light reduction structure and configured to move along the first axis and the second axis within the light reduction structure.

3. The system of claim 2, wherein the light reduction structure is further configured to substantially reduce ambient light from entering the quantum dot detection system.

4. The system of claim 1, wherein the controller is further configured to cause the support structure to move on the number of tracks.

5. The system of claim 3, wherein the controller is further configured to cause the quantum dot detection system to move along the first axis and the second axis.

6. The system of claim 1, wherein the connection system comprises:
    a plurality of suction cups configured to removably connect the number of tracks to the object; and
    a vacuum system configured to remove air from a volume bound by each of the plurality of suction cups and the object.

* * * * *